United States Patent [19]

Akkerboom et al.

[11] Patent Number: 5,211,958

[45] Date of Patent: May 18, 1993

[54] PHARMACEUTICAL COMPOSITION AND PROCESS FOR ITS PREPARATION

[75] Inventors: Piet J. Akkerboom, Zoetermeer; Robert De Cocq, Delft; Maria Wegman, Hoofddorp, all of Netherlands

[73] Assignee: Gist-Brocades, N.V., Delft, Netherlands

[21] Appl. No.: 877,385

[22] Filed: Apr. 29, 1992

Related U.S. Application Data

[63] Continuation of Ser. No. 655,210, Feb. 12, 1991, abandoned, which is a continuation of Ser. No. 278,020, Nov. 30, 1988, abandoned.

[30] Foreign Application Priority Data

Nov. 30, 1987 [EP] European Pat. Off. ........... 87202370

[51] Int. Cl.$^5$ .................................................. A61K 9/26
[52] U.S. Cl. .................................... 424/470; 424/465; 424/469
[58] Field of Search ................................. 424/470, 465

[56] References Cited

U.S. PATENT DOCUMENTS

| | | | |
|---|---|---|---|
| 4,292,299 | 9/1981 | Suzuki et al. | 424/16 |
| 4,454,108 | 6/1984 | Iida et al. | 424/16 |
| 4,665,081 | 5/1987 | Doi et al. | 514/356 |
| 4,753,801 | 6/1988 | Oren et al. | 424/465 |
| 4,837,030 | 6/1989 | Valarose, Jr. et al. | 424/489 |

FOREIGN PATENT DOCUMENTS

| | | |
|---|---|---|
| 0049061 | 4/1982 | European Pat. Off. . |
| 0073428 | 3/1983 | European Pat. Off. . |
| 0080862 | 6/1983 | European Pat. Off. . |
| 0159735 | 10/1985 | European Pat. Off. . |
| 0281200 | 9/1988 | European Pat. Off. . |
| 2518270 | 3/1976 | Fed. Rep. of Germany . |
| 2058565 | 4/1981 | United Kingdom . |
| 2172006 | 9/1986 | United Kingdom . |

OTHER PUBLICATIONS

The United States Pharmacopeia, Twentieth Revision, Official from Jul 1, 1980; Pharmaceutic Ingredients.

The Merek Index, p. 769.

"The Role of Swelling in the Disintegration Process", by C. Caramella et al., Int. J. Pharm. Tech. & Prod. Mfr., 5(2) 1–5, 1984, pp. 1–5.

Pharmaceutical Dosage Forms: Tablets, vol. 1, pp. 122–129.

G. Nagy, A. Keresztes, K. Pintye-Hodi, B. Selmeczi, and G. Kedvessy; "Untersuchungen uber die Textur und die Eigenschaften von Acetylsalicylsaure-Tabletten", Die Pharmazie 33, H. 11 (1978), pp. 747–749.

Handbook of Pharmaceutical Excipients, American Pharmaceutical Assoc. & The Pharmaceutical Society of GB, 1986, pp. 134–140.

"Identification and Analysis of Low Substituted Hydroxypropyl-cellulose (L-HPC)", Shin-Etsu Chemical, Technical Information, No. L-4, May 1976.

Martindale, 29th Ed., The Pharmaceutical Press, London, 1989, p. 1435.

Primary Examiner—Thurman K. Page
Assistant Examiner—Leon R. Horne
Attorney, Agent, or Firm—Keck, Mahin & Cate

[57] ABSTRACT

A multi-purpose pharmaceutical tablet which can either be readily swallowed or dissolved in water to give a dispersion, comprising a tetracycline, microcrystalline cellulose or microfine cellulose, low substituted hydroxypropylcellulose and a thickening agent, preferably hydroxypropyl methylcellulose, and optionally other conventional adjuvants. The tablet may be easily swallowed as such, and when immersed in water, it affords a very fine dispersion within 30–60 seconds. The tablet may be prepared by direct compression, or by a wet granulation process in which a granulate is used which contains tetracycline and any substantial amount of a wet binding substance.

24 Claims, No Drawings

PHARMACEUTICAL COMPOSITION AND PROCESS FOR ITS PREPARATION

This application is a continuation of application Ser. No. 07/655,210 filed Feb. 12, 1991, abandoned which is a continuation of Ser. No. 07/278,020 filed Nov. 30, 1988 abandoned.

The invention relates to a pharmaceutical composition, and more particularly to a tetracycline containing tablet, which exhibits rapid disintegration when immersed in water, and to a process for its preparation.

BACKGROUND OF THE INVENTION

It is generally known that the therapeutic action of a medicine in a living organism depends greatly upon the carrier by which the medicine is administered. High demands are made upon the pharmaceutical preparation, especially for drugs which are taken orally.

The first requirement is high bioavailability; that is, as much active substance as possible should be made available to the organism In the treatment of infections with an antibiotic-containing composition, which is the object of this invention, optimal blood levels of the antibiotic should be reached in the shortest possible time.

The second requirement is that the dosage form should be free from administration problems However, the dosage form with the best bioavailability is seldom easy to use and, conversely, one which is easily taken often does not have a satisfactory bioavailability.

Tablets are pharmaceutical formulations with several advantages. Tablets are easy to use with respect to dosing, storing, transporting and administering. However, many patients experience difficulties when swallowing a tablet and, moreover, the absorption of the active substance may be contingent on the dissolution rate of the tablet.

An aqueous solution or dispersion of the drug is easily ingested, is better absorbed by the patient and gives high initial blood concentrations However, a liquid is cumbersome to dose and to transport Moreover, it should often be prepared shortly before delivery to the patient, and stored at a low temperature. Sometimes preserving agents should be added to such a liquid preparation.

Therefore, so-called disperse tablets have been developed which, when immersed in water, rapidly disintegrate to provide a suspension of the drug, thus combining certain advantages of both dry and liquid dosage forms. Tablets of this type are described in European patent application EP-A-181650, German patent DE 1617343 and in J. Pharm. Pharmac. (1976), 28, 234-238. These known disperse tablets are not fully satisfactory, however, especially when directly ingested, because these tablets disintegrate already in the mouth into a pappy mass which is unpleasant to swallow. For some kinds of drugs, such as beta-lactam antibiotics improved types of disperse tablets have been developed, as described in European patent application EP-A-0281200.

Tetracyclines, especially doxycycline, are frequently prescribed medicines. However, no process is known for the preparation of tetracycline containing tablets which can either be easily swallowed, or quickly provide a fine dispersion when immersed in water.

SUMMARY OF THE INVENTION

It is, therefore, an object of this invention to provide a tetracycline containing tablet which can be used in two different ways. When immersed in water the tablet quickly disperses to provide an excellent, easy to ingest suspension. Alternatively, the tablet can be easily swallowed as such.

A further object of the invention is to provide a simple pharmaceutical process for the preparation of such tablets on an industrial scale. These objects are achieved by combining the tetracycline drug with certain adjuvants in a new composition. The tablet may be prepared using a wet granulation method or by direct compression.

DETAILED DESCRIPTION OF THE INVENTION

The tablet according to this invention contains at least a tetracycline, microcrystalline cellulose or microfine cellulose or a mixture of both, low-substituted hydroxypropylcellulose and a thickening agent.

Microcrystalline cellulose is the common name for purified, partially depolymerized cellulose occurring as a crystalline powder, composed of porous particles It is a widely used adjuvant, known, e.g., under the brand name AVICEL. Microfine cellulose (e.g. ELCEMA), also denoted as powdered 2 cellulose, is a mechanically processed -cellulose from fibrous plant materials. It is a common pharmaceutical binder and disintegrant.

In this description, "cellulose product" refers particularly to microcrystalline cellulose and microfine cellulose and to mixtures of them.

Microcrystalline cellulose or microfine cellulose is preferably used in amounts of 20–60 wt %, more preferably 35–50 wt % and particularly about 45 wt %. All percentages in this description and the appended claims are expressed as a percentage based on the amount of the tetracycline.

Low-substituted hydroxypropylcellulose acts as a disintegrant. This name denotes a common pharmaceutical excipient.

The thickening agent may be a natural gum, such as guar gum or gum arabic, or a cellulose derivative such as methylcellulose, ethylcellulose or hydroxyethylcellulose. The preferred thickening agent is hydroxypropyl methylcellulose, an adjuvant which is available in various viscosity grades. The contribution of the thickening agent to the viscosity should be low. Therefore, the viscosity of a 2% solution of the thickening agent in water, measured at 20° C., should be less than 50 centipoise (cps), preferably less than 10 cps and most preferably about 5 cps.

The thickening agent acts in conjunction with the low-substituted hydroxypropyl cellulose to provide the tablet with an accurately timed disintegration behavior. The tablet disintegrates at a rate which is sufficiently slow to permit it to be swallowed easily, but fast enough to give an excellent suspension in water within 60 seconds.

The low-substituted hydroxypropylcellulose and the thickening agent are preferably used in a total amount of 10–40 wt %, more preferably 20–30 wt %, and are present in weight ratios of low-substituted hydroxypropylcellulose to thickening agent of from 3:1 to 10:1. Particularly good results are obtained with a ratio of about 5:1.

Further conventional adjuvants, e.g. gliding agents such as silica gel and magnesium stearate, flavours and fillers such as lactose, starch and saccharin may also be added to the tablet composition.

A particularly suitable tetracycline is doxycycline, especially in the form of a hydrate, in particular the monohydrate, or in any other form having a sufficiently low solubility to be virtually tasteless Additional suitable tetracyclines are, for example, tetracycline trihydrate, oxytetracycline dihydrate and the calcium salt of chlorotetracycline.

The tablet according to the invention may be prepared by the usual direct compression method. However, doxycycline monohydrate occurs in different crystal forms, some of which give rise to serious tabletting problems due to bad flow and compression properties of the tabletting mixture.

Therefore, the invention further provides a tabletting method based on wet granulation, but using the ingredients of the direct compression recipe, which obviates this problem.

This preferred method comprises mixing the tetracycline with microcrystalline cellulose or microfine cellulose or a mixture of both, in amounts as defined hereinbefore, and adding 40–100 wt %, preferably 50–80 wt % of water, to obtain a wet mass, which is then granulated according to methods known in the art. The granules are then dried to a moisture content of preferably less than about 2 wt %, and passed through a sieve with small pores, preferably 0.71 mm. It should be noted that the granulate is made without using a substantial amount, i.e. 0–0.5 wt % and preferably 0–0.1 wt % of the usual wet binding substances, such as starch, sugars, polyvinylpyrrolidone (PVP) or cellulose esters. Surprisingly, a granulate of good quality is easily obtained.

The granulate is then mixed with low-substituted hydroxypropylcellulose and a thickening agent in amounts as defined hereinbefore to give a tabletable granulate of good flow, which, optionally with further adjuvants, can be easily compressed into tablets in the usual way.

The tablets according to the invention possess excellent properties. They can, at the patient's choice, either be swallowed as such or used in aqueous suspension, since they disperse, when immersed in water, often within 30–60 seconds, into a very fine suspension without leaving coarse granules.

The dispersion time is established (in duplo) by putting the tablet in a 100 ml glass containing 50 ml water at 20° C. After 30 sec. the contents are whirled until no lumps can be seen. The time is read and the dispersion is poured immediately through a 0.71 mm sieve, which should not retain any particle. The shortest time in which this condition is fulfilled is the dispersion time.

With respect to the speed and the amount of absorption of the tetracycline into the blood, the tablet of the invention and the suspension made from it are bio-equivalent.

It is further surprising that the inventive tablet exhibits its useful properties irrespective of whether it is prepared by direct compression or by the described wet granulation method. This feature contributes substantially to the flexibility of the manufacturing process.

The following examples will serve as illustrations and should not be construed as limiting the invention.

EXAMPLE 1

Doxycycline monohydrate (105.8 g) and microcrystalline cellulose (45 g) are mixed for 15 minutes in a planetary mixer. The mixture is then granulated with 60 ml of water. After 10 minutes of kneading, the obtained wet mass is passed through a 2 mm sieve and the wet granulation dried at about 40° C. until its water content is below 2% by weight. The granulate is then passed through a 0.71 mm sieve and is mixed for 20 minutes with low-substituted hydroxypropylcellulose LH11 (18 g), hydroxypropyl methylcellulose 5 cps viscosity(4 g), saccharin (10 g), colloidal silica (0.6 g) and enough lactose to bring the total weight of the mixture to 248 g. Then magnesium stearate (2 g) is added and the mixing is continued for an additional 2 minutes. The resulting mixture is compressed into tablets, each of about 250 mg, about 9 mm diameter and a hardness of 70–100 N, or into tablets, each of about 125 mg having a hardness of 60–90 N. The tablets disintegrate completely in water at room temperature within 30–45 sec.

EXAMPLE 2

The components of the previous example, with the exception of water and magnesium stearate, are mixed for 20 minutes. Magnesium stearate (2 g) is added and mixing is continued for an additional 2 minutes. The resulting mixture is compressed into tablets as described in the previous example. The resulting tablets exhibit the same pharmaceutical properties as the tablets of the previous example.

EXAMPLE 3

Following the same procedure as described in Example 1, 111 g of oxytetracycline dihydrate is granulated with 80 ml of water. Tablets of 250 mg each are compressed in the usual way. The resulting tablets have a disintegration time of 30 sec and a hardness of 80 N.

EXAMPLE 4

Doxycycline monohydrate (11 g), microcrystalline cellulose (4.5 g), low-substituted hydroxypropyl cellulose (2.5 g), hydroxypropyl methylcellulose of 5 cps viscosity (0.75 g), saccharin (1 g), maize starch (0.075 g), lactose (4.16 g) and colloidal silica (0.188 g) are mixed together for 20 minutes. Magnesium stearate (0.15 g) is added and mixing continued for an additional 2 minutes. The resulting mixture is compressed into tablets of about 250 mg with a diameter of about 9 mm and a hardness of 70–100 N. The tablets disintegrate completely in water at room temperature within 45–60 sec.

EXAMPLE 5

The procedure of Example 4 is repeated except that 4.5 g of microfine cellulose is used instead of 4.5 g of microcrystalline cellulose. The resulting tablets have a hardness of 90–110 N and disintegrate in water at room temperature within 100 sec.

What is claimed is:

1. A pharmaceutical tablet, comprising:
   tetracycline;
   a cellulose produce selected from the group consisting of microcrystalline cellulose, microfine cellulose and mixtures thereof;
   low-substituted hydroxypropylcellulose; and
   a thickening agent selected from the group consisting of natural gums and cellulose derivatives, and having a viscosity of less than 50 cps, measured as a 2% by weight aqueous solution at 20° C. wherein the weight ratio of low-substituted hydroxypropylcellulose to the thickening agent is between 3:1 and 10:1, and the cellulose product is present in an amount of 20–60 wt % based on the weight of the tetracycline.

2. The tablet of claim 1, wherein the thickening agent in a 2% by weight aqueous solution at 20° C. has a viscosity of less than 10 cps.

3. The tablet of claim 1, wherein the thickening agent in a 2% by weight aqueous solution at 20° C. has a viscosity of about 5 cps.

4. The tablet of claim 1, wherein the thickening agent is hydroxypropyl methylcellulose.

5. The tablet of claim 1, wherein the low-substituted hydroxypropylcellulose and the thickening agent together amount to 10–40 wt % based on the weight of the tetracycline.

6. The tablet of claim 1, wherein the low-substituted hydroxypropylcellulose and the thickening agent together amount to 20–30 wt % based on the weight of the tetracycline.

7. The tablet of claim 1, wherein the weight ratio of low-substituted hydroxypropylcellulose to the thickening agent is about 5:1.

8. The tablet of claim 1, wherein the cellulose product is present in an amount of 35–50 wt % based on the weight of the tetracycline.

9. The tablet of claim 1, wherein after placing the tablet in water of at least 20° C., the tablet has a disintegration time of between 30 and 100 seconds and provides a smooth dispersion, free of coarse lumps.

10. A pharmaceutical tablet, comprising:
   tetracycline;
   a cellulose product selected from the group consisting of microcrystalline cellulose, microfine cellulose and mixtures thereof;
   low-substituted hydroxypropylcellulose; and
   a thickening agent selected from the group consisting of natural gums and cellulose derivatives, and having a viscosity of less than 10 cps in a 2% by weight aqueous solution at 20° C.
wherein the cellulose product is present in an amount of 20–60 wt % based on the weight of the tetracycline, wherein the low-substituted hydroxypropylcellulose and the thickening agent together amount to 10–40 wt % based on the weight of the tetracycline, and the weight ratio of the low-substituted hydroxypropylcellulose to the thickening agent is between 3:1 and 10:1.

11. A process for the preparation of a pharmaceutical tablet of controlled disintegrating by direct compression, comprising the step of:
   making an intimate mixture of tetracycline; a cellulose product selected from the group consisting of microcrystalline cellulose, microfine cellulose and mixtures thereof; low-substituted hydroxypropylcellulose; and a thickening agent selected from the group consisting of natural gums and cellulose derivatives, and having a viscosity of less than 50 cps, measured as a 2% by weight aqueous solution at 20° C. wherein the weight ratio of low-substituted hydroxypropylcellulose to the thickening agent is between 3:1 and 10:1, and the cellulose product is present in an amount of 20–60 wt % based on the weight of the tetracycline; and
   compressing the intimate mixture into tablets.

12. The process of claim 11, wherein the thickening agent in a 2% by weight aqueous solution at 20° C. has a viscosity of less than 10 cps.

13. The process of claim 11, wherein the thickening agent is hydroxypropyl methylcellulose.

14. The process of claim 11, wherein the low-substituted hydroxypropylcellulose and the thickening agent together are added in an amount of 10–40 wt % based on the weight of the tetracycline.

15. The process of claim 11, wherein the low-substituted hydroxypropylcellulose and the thickening agent together are added in an amount of 20–30 wt % based on the weight of the tetracycline.

16. A process for the preparation by wet granulation of a pharmaceutical tablet comprising tetracycline; a cellulose product selected from the group consisting of microcrystalline cellulose, microfine cellulose and mixtures thereof; low-substituted hydroxypropylcellulose; and a thickening agent selected from the group consisting of natural gums and cellulose derivatives, and having a viscosity of less than 50 cps, measured as a 2% by weight aqueous solution at 20° C. wherein the weight ratio of low-substituted hydroxypropylcellulose to the thickening agent is between 3:1 and 10:1, and the cellulose product is present in an amount of 20–60 wt % based on the weight of the tetracycline, comprising the steps of:
   a) mixing the tetracycline and the cellulose product with water to form a wet mass;
   b) processing the wet mass of step a) to form a granulate;
   c) passing the granulate of step b) through a first woven wire screen;
   d) drying the sieved granulate of step c);
   e) passing the dried granulate of step d) through a second woven wire screen;
   f) collecting the resulting granulate of step e);
   g) mixing the granulate with the low-substituted hydroxypropylcellulose and thickening agent to form an intimate mixture; and
   h) compressing the intimate mixture of step g) into tablets.

17. The process of claim 16, wherein 40–100 wt % of water, based on the weight of the tetracycline, is used.

18. The process of claim 16, wherein 50–80 wt % of water, based on the weight of the tetracycline, is used.

19. The process of claim 16, wherein the granulate contains 0.5 wt % or less of a wet binding substance.

20. The process of claim 16, wherein the granulate contains 0.2 wt % of less of a wet binding substance.

21. The process of claim 16, wherein the thickening agent in a 2% by weight aqueous solution at 20°0 C. has a viscosity of less than 10 cps.

22. The process of claim 16, wherein the thickening agent is hydroxypropyl methylcellulose.

23. The process of claim 16, wherein the low-substituted hydroxypropylcellulose and the thickening agent together are added in an amount of 10–40 wt % based on the weight of the tetracycline.

24. The process of claim 16, wherein the low-substituted hydroxypropylcellulose and the thickening agent together are added in an amount of 20–30 wt % based on the weight of the tetracycline.

* * * * *

UNITED STATES PATENT AND TRADEMARK OFFICE
CERTIFICATE OF CORRECTION

PATENT NO. : 5,211,958
DATED : May 18, 1993
INVENTOR(S) : Piet J. AKKERBOOM et al.

It is certified that error appears in the above-identified patent and that said Letters Patent is hereby corrected as shown below:

On the title page, item [75], change Inventors name as follows:

"Maria Wegman" should read --Bernardus Wegman--.

IN THE CLAIMS:

Col. 6, claim 20, line 2, change "0.2 wt " of" to --0.1 wt % or--

Col. 6, claim 21, line 2, change "20°0C" to --20°C--

Signed and Sealed this

Eighteenth Day of January, 1994

Attest:

BRUCE LEHMAN

*Attesting Officer*     *Commissioner of Patents and Trademarks*